United States Patent [19]

Trudell

[11] Patent Number: 5,449,338
[45] Date of Patent: Sep. 12, 1995

[54] MODULAR ORTHOPEDIC BRACE
[75] Inventor: Thomas G. Trudell, Winter Park, Fla.
[73] Assignee: Dobi-Symplex, Apopka, Fla.
[21] Appl. No.: 133,500
[22] Filed: Oct. 7, 1993
[51] Int. Cl.[6] .................................................. A61F 5/02
[52] U.S. Cl. ............................................ 602/19; 602/5
[58] Field of Search ....................... 602/5, 19, 1, 12, 16, 602/20; 2/44, 45

[56] References Cited

U.S. PATENT DOCUMENTS 5,012,798  5/1991  Graf et al. .............................. 602/19

FOREIGN PATENT DOCUMENTS 234372   9/1987  European Pat. Off. ............. 602/19
1725876  4/1992  U.S.S.R. ................................ 602/19

Primary Examiner—Richard J. Apley
Assistant Examiner—Beverly A. Meindl
Attorney, Agent, or Firm—Stroock & Stroock & Lavan

[57] ABSTRACT

An adjustable modular off the shelf orthopedic brace for recumbent treatment of scoliosis includes an anterior upright and a posterior upright. A plurality of lateral shells are adjustably supported between the uprights. A plurality of connecting plates each affixed to a respective shell adjustably connects each shell to at least one of the anterior upright and posterior upright and allows for the adjustment of the positioning of the lateral shells along the anterior upright and posterior upright. Additionally, the plates allow for adjustment of the angular positioning and lateral positioning of the lateral shells relative to the anterior and posterior uprights.

8 Claims, 5 Drawing Sheets

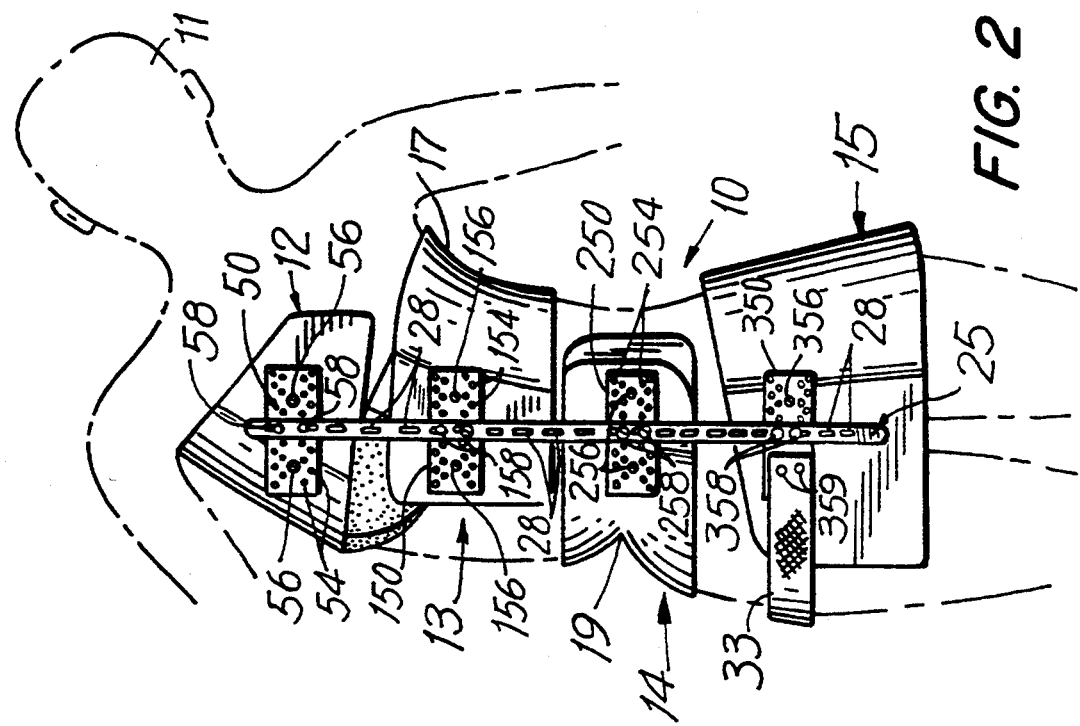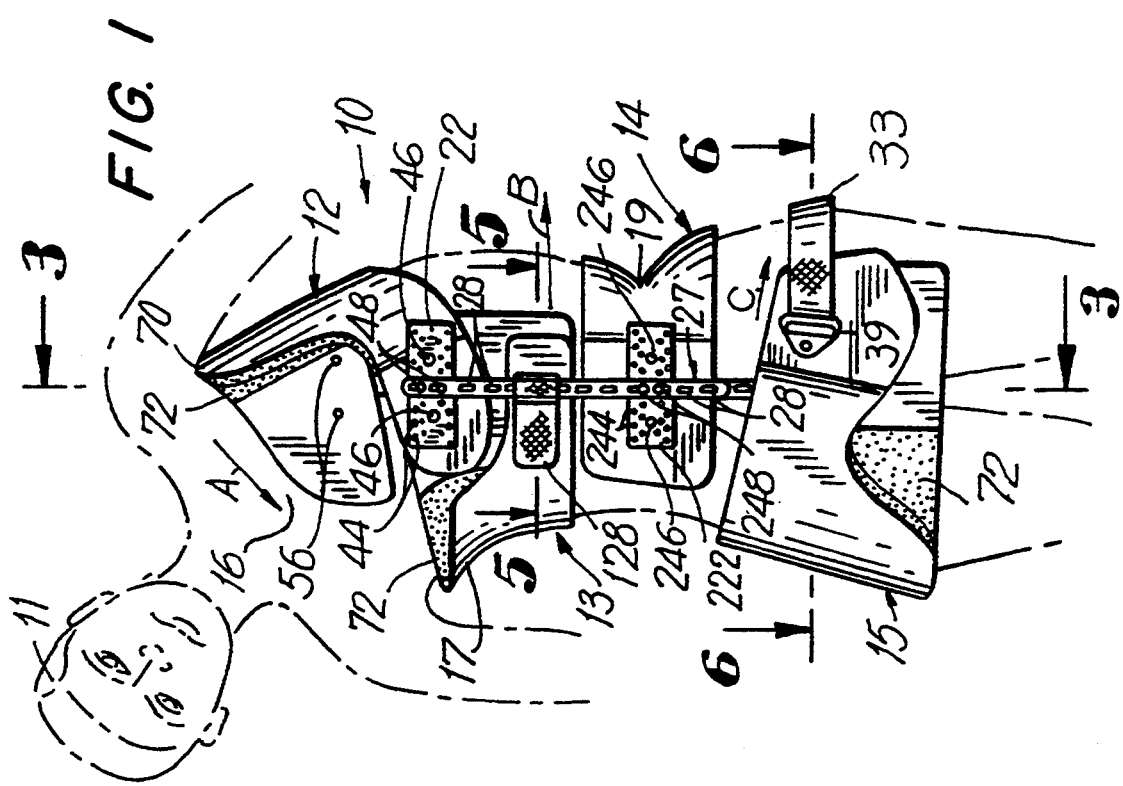

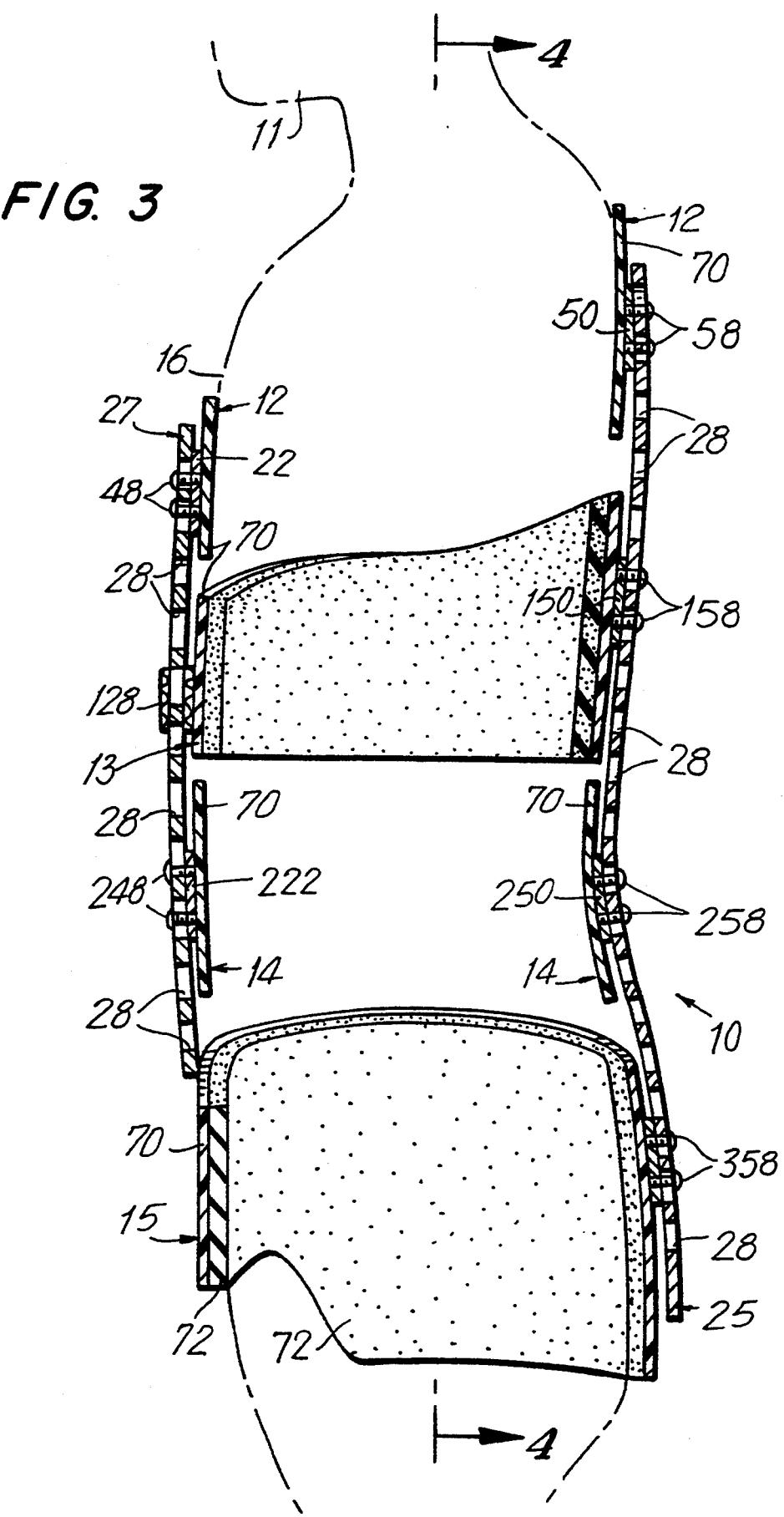

MODULAR ORTHOPEDIC BRACE

BACKGROUND OF THE INVENTION

The present invention relates to an orthopedic brace and especially to an adjustable, modular bending brace for treating lateral curvature of the spine or scoliosis.

A wide variety of orthopedic appliances for treatment of various conditions, including orthopedic braces for the treatment of scoliosis are known in the art. One such system employs a girdle or corset fitted to the wearer's body and positioned around the pelvis and chest, with appropriate attachments for the neck. Another prior structure employs a prefabricated girdle to which the super-structure may be attached. One prior apparatus is known from U.S. Pat. No. 3,945,376 and utilizes various bars and straps joined by a rigid pelvic band positioned about the hips of the wearer and flexible iliac crest members on each side at the crest or top of the pelvic structure. A scoliosis brace known from U.S. Pat. No. 2,687,129 treats lateral curvature of the spine and joins a hip pad and chest pad with straps around the patient's body and over his shoulder, and allows for an adjustable tension means for engaging the body tangentially to the point of greatest convexity of the spine. In U.S. Pat. No. 4,285,336 a scoliosis orthotic system has an anterior panel and a pair of posterior panels connected by pelvic bands and iliac crest members. U.S. Pat. No. 3,878,841 shows an adjustable supportive and dynamic orthotic device for raising and supporting the shoulder of a surgical patient, while U.S. Pat. No. 1,935,859 shows an orthopedic appliance for the treatment of scoliosis having a plurality of adjustable pads interconnected to the body of the patient. In U.S. Pat. No. 4,688,558 an orthopedic full body brace for the treatment of scoliosis is worn only while the patient is asleep or in a lying position and utilizes two interconnected shells conforming to a desired bending angle to apply a correcting force directly to the spine.

These devices have been satisfactory. However, they suffer from the disadvantage that the shells and panels are not adjustable. Until now, orthotists have been forced to custom-order the braces and appliances for each patient based on casts and measurements. Whenever a patient grew or progressed, a new brace had to be custom ordered based on a new set of casts and measurements. Each brace required time and money to produce and deliver. Accordingly, an adjustable off the shelf brace which overcomes the shortcomings of the prior art is desired.

SUMMARY OF THE INVENTION

Generally speaking, the present invention relates to orthopedic braces and especially to an adjustable, modular brace for recumbent treatment of scoliosis including the use of flexible lateral shells curved and connected together to cover much of the patient's bodice, extending from the hips to the arm pits. The shells are available in a range of types and sizes, which can be combined variously to suit each patient's individual needs. The shells are mounted between an anterior upright and posterior upright. An adjustment plate provided on each shell selectively couples the shell to the anterior upright and/or posterior upright and allows for adjustment of the height of each shell relative to the uprights while allowing for lateral and angular adjustment of the shell relative to the uprights. The orthopedic apparatus applies a force opposite the lateral curvature of the spine of a scoliosis patient by forcing the patient to bend in a direction opposite to the patient's spinal curvature.

An object of the present invention is to provide an improved orthopedic bending brace.

Another object of the invention is to provide an orthopedic bending brace which may be adapted from off the shelf parts to accommodate a variety of patients without requiring the casting of each individual brace.

Yet another object of the invention is to provide a bending brace which may accommodate patient growth and which may be adjusted to apply different bending forces at different times.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description, taken in connection with the accompanying drawings, in which:

FIG. 1 is a front elevational view of an orthopedic brace placed on a patient in accordance with the present invention;

FIG. 2 is a rear elevational view of the apparatus of FIG. 1;

FIG. 3 is a sectional view along the line 3—3 of FIG. 1;

DESCRIPTION OF THE PREFERRED EMBODIMENT

Reference is made to the drawings, wherein a modular orthopedic bending brace, generally indicated as 10, is illustrated for treating a person 11 having scoliosis or lateral curvature of the spine. The apparatus is specifically directed toward a rigid body brace for treating scoliosis in a person in a lying position, such as when the person is asleep. It is not worn during daylight hours when the person is actively pursuing daily activities.

Figure 4:
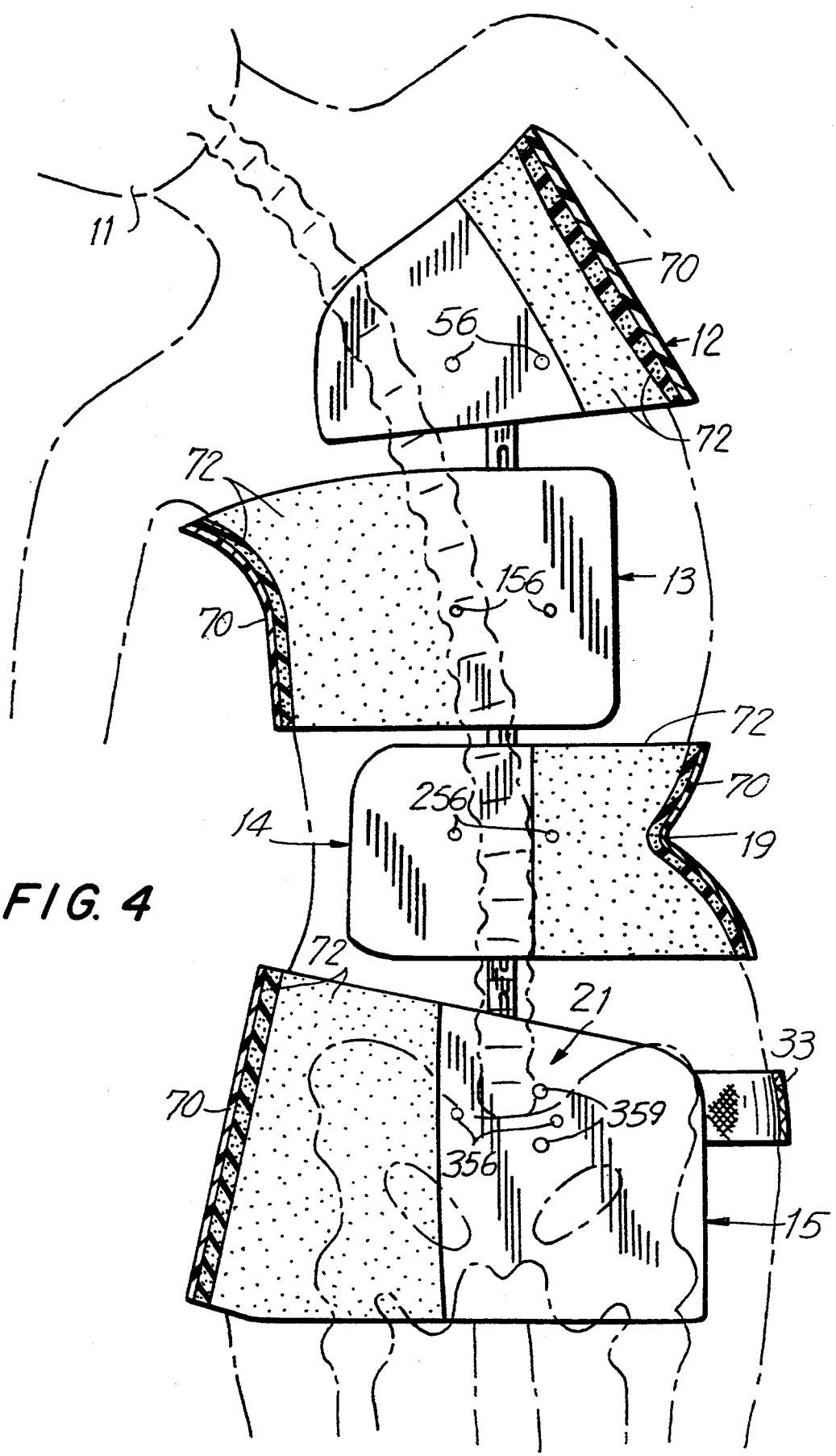
FIG. 4 is a sectional view along the line 4—4 of FIG. 3.

Orthopedic brace 10 has a posterior upright 25 and an anterior upright 27, a first flexible lateral shell 12 (unbend shell), a second flexible lateral shell 13 (lateral shift), a third flexible lateral shell 14 (lumbar stabilization) and a fourth flexible lateral shell 15 (secondary unbend) are adjustably mounted between anterior upright 27 and posterior upright 25. Anterior upright 27 and posterior upright 25 are each formed with a plurality of slots 28 therein. As shown in FIG. 4, shells 12 and 14 have an inner curvature shaped to provide a bending force at one side of the person's body, while shells 13 and 15 have an inner curvature shaped to fit across the opposed side of the person's body.

Unbend shell 12 is substantially U-shaped to fit high on the upper rib cage and chest 16 and to provide an unbend force at the top of chest 16 in the general direction of arrow A (FIG. 1). An adjustment plate 22 is affixed to unbend shell 12 on an anterior portion thereof. Adjustment plate 22 is formed with a plurality of holes 44 therein. Adjustment plate 22 is attached to shell 12 by screws 46 which pass through at least two of holes 44. A pair of screws 48 affix adjustment plate 22, and in turn shell 12, to anterior upright 27.

A second adjustment plate 50 is affixed to unbend shell 12 at a posterior portion of unbend shell 12. Adjustment plate 50 is formed with a plurality of holes 54 therein and is attached by screws 56 passing through at least two of holes 54. A pair of screws 58 affix adjustment plate 50 to posterior upright 25.

Screws 48 and 58 attach to respective uprights 25, 27 passing through slots 28. The height of unbend shell 12 is adjusted relative to posterior and anterior uprights 25, 27 by selecting which individual slot 28 is to receive screw pairs 48, 58. Additionally by attaching adjustment plates 22, 50 utilizing different holes 44, 54 it is possible to adjust the medial and lateral positioning of shell 12 relative to posterior and anterior uprights 25, 27. As a result a single unbend shell 12 may be adjusted to accommodate a plurality of different patients, the growth over time in a single patient, and the desire to change the angle of unbend force without recasting a new brace.

Lateral shift shell 13 has a concave arcuate portion 17 and fits lower on the rib cage and chest 16 than unbend shell 12 at an opposed side of chest 16. Shell 13 provides a lateral shift force against chest 16 in the direction of arrow B. As with shell 12, an adjustment plate 150 formed with a plurality of holes 154 therein is affixed to a posterior portion of shell 13 by screws 156. A pair of screws 158 are received through slots 28 of posterior upright 25 to affix adjustment plate 150 to posterior upright 25.

Figure 5:
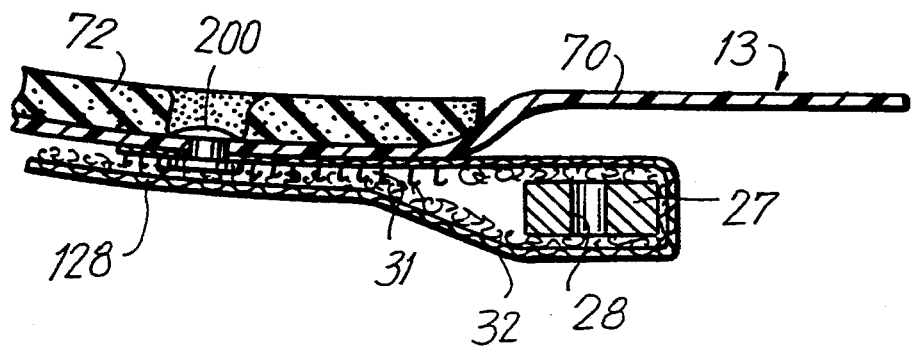
FIG. 5 is a sectional view along the line 5—5 of FIG. 1.

A strap 128, having hooks 31 formed on a portion thereof and a dense pile 32 formed on another portion thereof, is affixed to an anterior portion of shell 13 by rivets 200. Strap 128 loops around anterior upright 27 (FIG. 5) and fastens upon itself by a nylon hook 31 grabbing dense pile 32 to anchor shell 13 to anterior upright 27.

Shell 13 may also be adjusted to accommodate a plurality of different patients, the growth over time of a single patient and to change the forces being applied by adjusting the position of shell 13 utilizing screws 156 and 158.

Shell 14 has an arcuate portion 19 and fits between the iliac portion 20 and the upper chest portion 16 of person 11. Shell 14 is shaped to be anchored above the pelvic bone and provides a lumbar stabilization force. An adjustment plate 222 having a plurality of holes therein 244 is affixed at the outer anterior portion of shell 14. Adjustment plate 222 is attached to shell 14 by screws 246. A pair of screws 248 affix adjustment plate 222 to anterior upright 25. Similarly, adjustment plate 250 having a plurality of holes 254 is affixed to a posterior portion of lumbar stabilization shell 14 by screws 256. Screws 258 affix adjustment plate 250 to posterior upright 27. As a result shell 14 may also be adjusted to accommodate a plurality of different patients, the growth over time of a single patient, and to change the forces being applied.

Shell 15 is formed as a U-shaped member and fits low over the iliac portion 21 of a person 11. Shell 15 provides a secondary unbend force substantially the direction of arrow C (FIG. 1). An adjustment plate 350 having a plurality of holes 354 formed therein is attached by screws 356 to a posterior portion of secondary unbend shell 15. A pair of screws 358 affix adjustment plate 350 to posterior upright 27 through slots 28.

Figure 6:
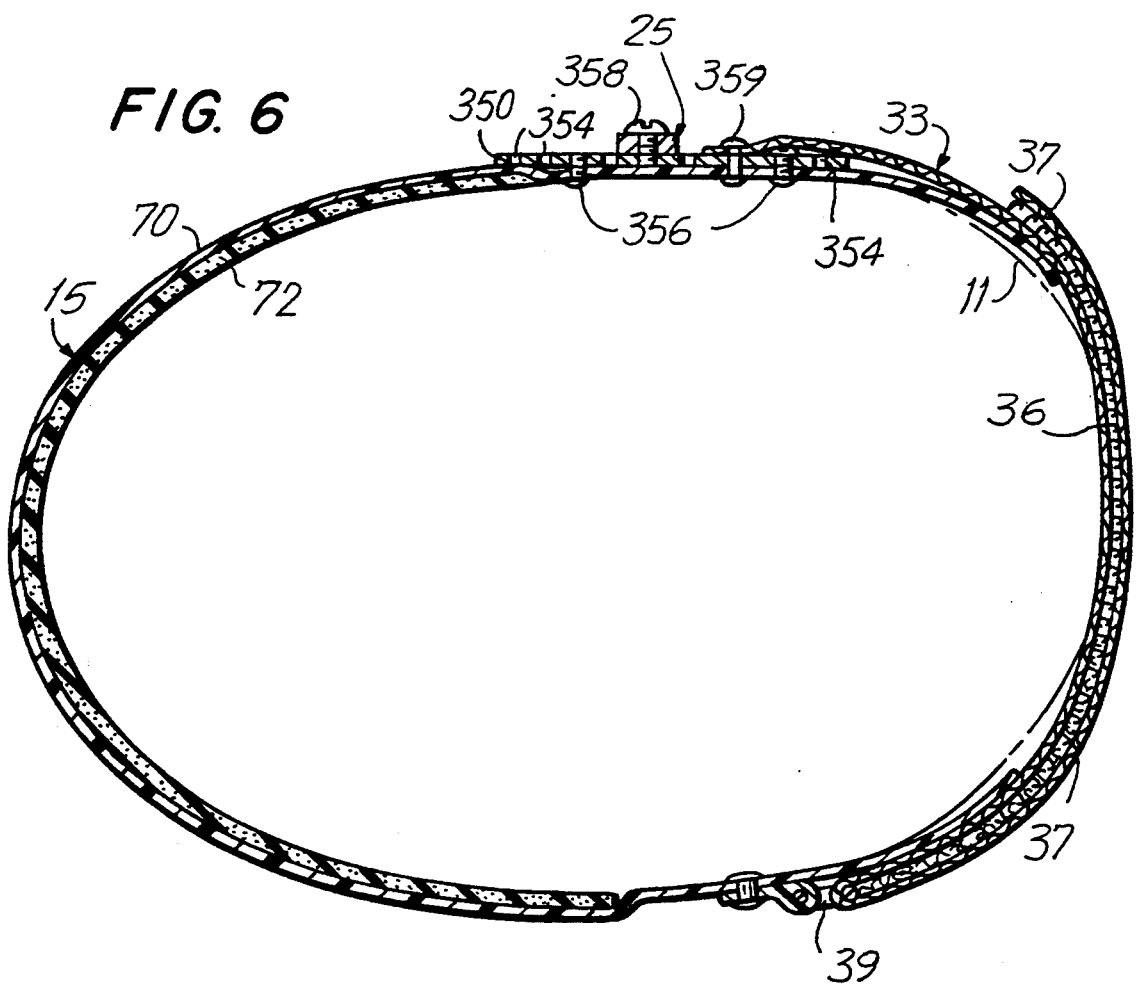
FIG. 6 is a sectional view along the line 6—6 of FIG. 1.
Figure 7:
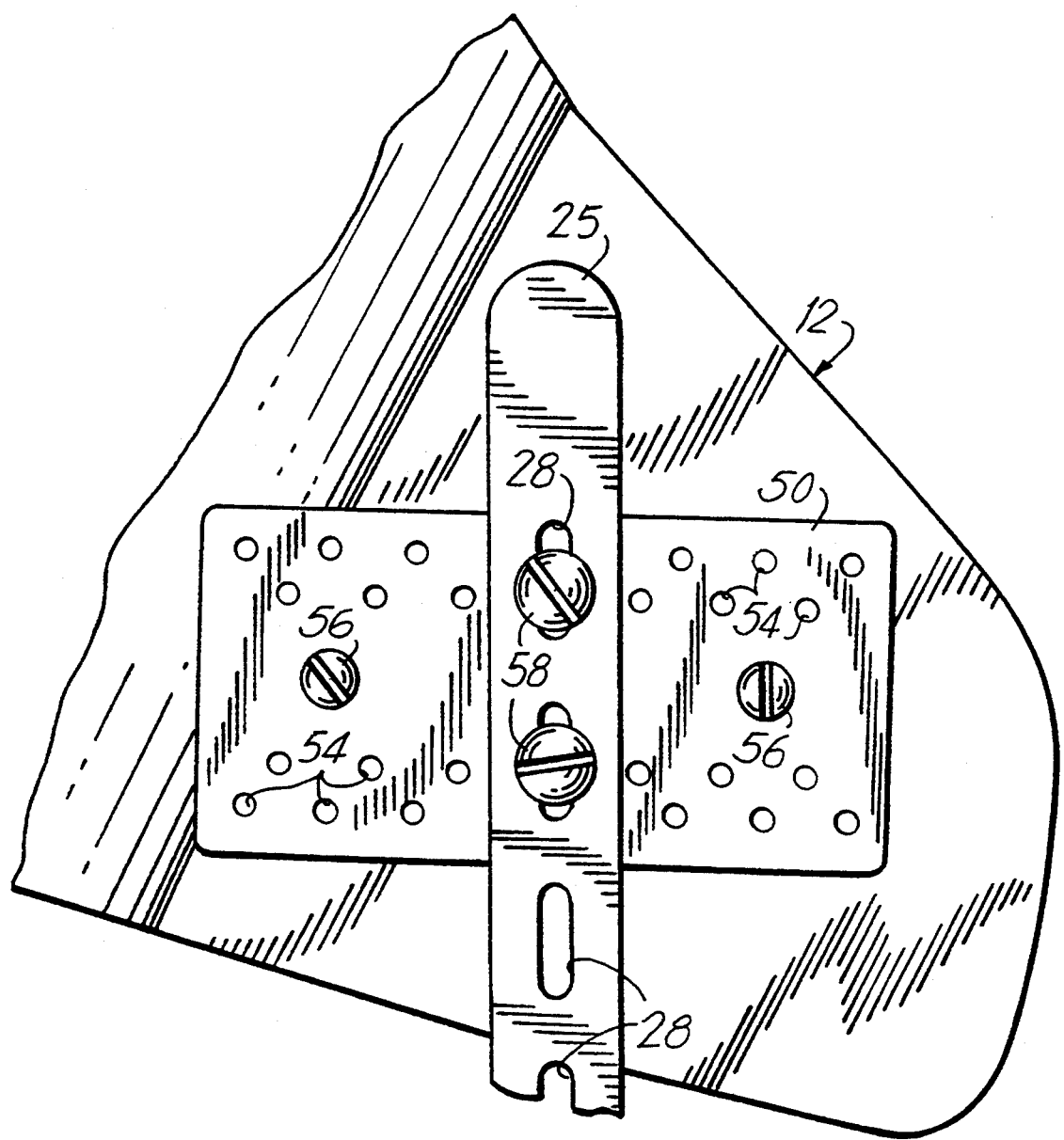
FIG. 7 is an enlarged front elevational view of an adjustment plate constructed in accordance with the invention.

A strap 33 is attached to plate 350 by rivets 359 as shown in FIG. 6. Strap 33 has first portion formed of tiny nylon hooks 36 and a second portion formed of dense nylon pile 37 so as to secure against itself. A D-ring 39 is affixed to the anterior lateral edge of shell 15. Strap 33 is dimensioned to pass through D-ring 39 and loop upon itself so that hooks 36 secure nylon pile 37 to secure shell 15 about person 11.

In the preferred embodiment shells 12, 13, 14, 15 are made of a two layer construction molded to the particular shapes shown. An outer layer 70 of each shell is formed of rigid yet flexible plastic such as a high density polyethylene which provides sufficient rigidity to produce the desired bending forces while remaining flexible enough to provide enough "give" to allow a patient to apply and remove the device. An inner layer 72 is formed from a closed cell foam to provide a protective cushion between the patient and hard outer shell 70. The positioning and shapes of each shell allow the body to be held in a position to force the spine in a position as shown in FIG. 4 against the normal curvature of the scoliosis patient's spine. Thus the interior curvature of the bending shell 12 is shaped to force the body to be held in a curved position against an area braced by secondary unbending shell 15 and the rib cage area braced by lateral shift brace 13. Additionally, posterior upright 25 exhibits a concave curve towards the spine (FIG. 3) and anterior brace 27 provides a slight convex curve away from the spine.

An orthotist will stock a supply of shells 12, 13, 14, 15 and posterior and anterior uprights 25, 27 on site. The shells will each be stocked in three anterior to posterior widths corresponding to small medium and large. A patient will be measured, the degree and type of correction bending will be determined and a brace will be fashioned by the orthotist on site using the off the shelf uprights and shells.

To form the modular bending brace a posterior upright 25 and anterior upright 27 are taken from stock. An appropriately sized stabilization shell 14 and adjustment plates 222, 250 are taken from stock. Based upon the measurements the relative medial lateral and positioning angle of shell 14 is determined. Screws 246 are inserted through appropriate holes 244 of adjustment plate 222 and screws 256 are inserted through appropriate holes 254 to provide the appropriate orientation of shell 14 relative to posterior upright 27 and anterior upright 25. The height of shell 14 is set by passing screws 248, 258 through appropriate slots 28 of posterior and anterior uprights 25, 27.

This process is repeated for each shell 13, 12 and 15 in that order so that each shell is properly positioned along posterior upright 25 and anterior upright 27, and each shell 13, 14, 15 is properly oriented to provide the desired bending forces.

During use, velcro straps 33, 128 are opened and unattached to anterior upright 27. Brace 10 is then slipped onto the body of patient 11 by inserting the patients body through the open end of shells 12–15. Because shells 12–15 are formed of a flexible polyethylene the anterior and posterior shell surfaces can be separated from each other providing clearance to receive the patient's body. Strap 128 is then looped about anterior upright 27 and tightly secured against itself to prevent movement of lateral shift shell 13. Strap 33 is passed through D-ring 39 and looped upon itself so that hooks 36 secure nylon pile 37 to secure shell 15 about person 11.

As the patient grows they do not outgrow brace 10. The size, height, and separation of each shell 12–14 may be adjusted to accommodate growth by placing screws 58, 158, 258 and 358 in different slots 28 of posterior uprights 25 and placing screws 48 and 248 in different slots 28 of anterior upright 27. The medial lateral positioning of each shell can be adjusted by moving each positioning plate relative to the shell and the angle of orientation is adjusted by placing the adjustment plate fastening screws (46 by way of example) in different holes of the adjustment plate than previously used. Each shell may be positioned independently of another as needed.

The brace can be rapidly attached and easily removed by the unstrapping of straps 128 and 33 and the opening of flexible lateral shells 13 and 15 from the side. Shells 13 and 15 have enough give to allow patient 11 to slide in and out of orthopedic brace 10. The straps being located on the front and side of brace 10 allow patient 11 to quickly loop the straps and pull them tight to apply the necessary bending force for the corrective action to the patient's spine. In this embodiment a correction being provided in the direction of arrow A. However, it is readily understood that by reversing the position of the shells a correction force may be provided in the opposite direction so that the brace has the capability of correcting both right handed and left hand spinal curvatures. Additionally, this embodiment utilizes four shells. However, it is contemplated that the lumbar stabilization shell and secondary unbend shell may be replaced by a single trochanter or lumbar stabilization shell so that only three shells need be used to correct certain spinal curvatures.

By providing a bending brace formed of at least three adjustable modular shells supported between two uprights an off the shelf brace which can be adjusted to fit a variety of patients without the need for casting special parts is provided. Additionally, by providing slots within each upright the same brace may be continuously used even as the patient grows. By using adjustment plates, having a plurality of holes therein, which position the shell relative to the uprights a single brace may be adjusted and used to accommodate changing angles of required force, removing the need to recast or remold the brace each time there is a physical change in the patient or a change in the treatment.

It will thus be seen that the objects set forth above, among those made apparent from the preceding description, are efficiently attained and, since certain changes may be made in the above construction without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An adjustable modular bending brace for treatment of scoliosis comprising:
    an anterior upright means formed as a unitary structure;
    a posterior upright means formed as a unitary structure;
    a plurality of lateral shells; and
    connecting means for adjustably fixedly connecting each lateral shell to at least one of said anterior upright means and posterior upright means at one of a plurality of positions fixed relative to said anterior upright means and posterior upright means, said connecting means selectively adjusting the positioning of said lateral shells along the lengthwise extent of said anterior upright means and posterior upright means at one of said plurality of fixed positions.

2. The orthopedic brace of claim 1, wherein said connecting means includes a plurality of slots formed along said anterior upright means and posterior upright means and at least a respective pair of screws coupled to a respective shell and adapted to be received within said slots.

3. The orthopedic brace of claim 1, wherein said connecting means positions each said shell independently of another said shell.

4. The orthopedic brace of claim 1, wherein said connecting means includes fastening means for fastening a lateral shell to the connecting means and for adjusting the lateral positioning of the lateral shells relative to said anterior upright means.

5. An adjustable modular bending brace for treatment of scoliosis comprising:
    an anterior upright means;
    a posterior upright means;
    a plurality of lateral shells; and
    connecting means for adjustably connecting each lateral shell to at least one of said anterior upright means and posterior upright means, said connecting means adjusting the positioning of said lateral shells along the lengthwise extent of said anterior upright means and posterior upright means, said connecting means including fastening means for fastening a lateral shell to the connecting means and for adjusting the lateral positioning of the lateral shells relative to said anterior upright means, the fastening means further adjusting the angular positioning of the lateral shells relative to said anterior upright means.

6. An adjustable modular bending brace for treatment of scoliosis comprising:
    an anterior upright means;
    a posterior upright means;
    a plurality of lateral shells; and
    connecting means for adjustably connecting each lateral shell to at least one of said anterior upright means and posterior upright means, said connecting means adjusting the positioning of said lateral shells along the lengthwise extent of said anterior upright means and posterior upright means, said connecting means including fastening means for fastening a lateral shell to the connecting means and for adjusting the lateral positioning of the lateral shells relative to said anterior upright means, said fastening means including an adjustment plate with a plurality of holes formed therein, at least two screws to be received by a pair of said holes, each pairing of said holes defining a lateral position and angle of orientation of said shell relative to said anterior upright means.

7. The adjustable modular bending brace of claim 1, wherein at least one of said lateral shells applies a bending force against a user's body.

8. An adjustable modular bending brace for treatment of scoliosis comprising:

an anterior upright means;

a posterior upright means;

a plurality of lateral shells each shell providing a force against a user's body; and fastening means for fastening a lateral shell to at least one of the anterior upright means and posterior upright means, the fastening means adjusting the angular positioning of the lateral shells relative to the anterior upright means.

* * * * *